US008556835B2

(12) United States Patent
Ferber et al.

(10) Patent No.: US 8,556,835 B2
(45) Date of Patent: Oct. 15, 2013

(54) MASSAGE APPARATUS WITH HEATER

(75) Inventors: Roman Ferber, West Bloomfield, MI (US); Mordechai Lev, West Bloomfield, MI (US); Shianp Jyh Chung, Taipei (TW)

(73) Assignee: FKA Distributing Co., Commerce Township, MI (US)

( * ) Notice: Subject to any disclaimer, the term of this patent is extended or adjusted under 35 U.S.C. 154(b) by 389 days.

(21) Appl. No.: 12/740,026

(22) PCT Filed: Nov. 5, 2007

(86) PCT No.: PCT/US2007/083604
§ 371 (c)(1),
(2), (4) Date: Dec. 27, 2010

(87) PCT Pub. No.: WO2009/061309
PCT Pub. Date: May 14, 2009

(65) Prior Publication Data
US 2011/0105964 A1    May 5, 2011

(51) Int. Cl.
*A61H 1/00* (2006.01)
*A61F 7/00* (2006.01)
(52) U.S. Cl.
USPC .................. 601/18; 601/15; 601/84; 607/96
(58) Field of Classification Search
USPC ............. 601/15, 18, 19, 84, 97–99, 101, 102, 601/103, 107, 108, 112, 113, 115, 116, 118, 601/122, 126, 134; 607/80, 88, 96
See application file for complete search history.

(56) References Cited

U.S. PATENT DOCUMENTS

| 4,604,993 | A | * | 8/1986 | Moriwaki et al. ............... 601/18 |
| 5,336,159 | A | | 8/1994 | Cheng |
| 5,486,156 | A | | 1/1996 | Takach |
| 5,703,901 | A | * | 12/1997 | Ohtani et al. .................. 373/109 |
| 6,149,611 | A | | 11/2000 | Chen |
| 6,454,732 | B1 | | 9/2002 | Lee |
| 6,511,446 | B1 | * | 1/2003 | Wu ................................ 601/15 |
| 6,744,370 | B1 | * | 6/2004 | Sleichter et al. ............... 340/576 |
| 7,128,721 | B2 | | 10/2006 | Ferber et al. |
| 7,128,722 | B2 | | 10/2006 | Lev et al. |
| 7,532,926 | B2 | * | 5/2009 | Bernabei ........................... 607/3 |

(Continued)

OTHER PUBLICATIONS

Chinese Office Action for corresponding Application No. 200780102073.X, mailed May 3, 2012, 6 pages.

(Continued)

*Primary Examiner* — Justine Yu
*Assistant Examiner* — LaToya M Louis
(74) *Attorney, Agent, or Firm* — Brooks Kushman P.C.

(57) ABSTRACT

A massage apparatus is provided with a housing, and a substrate mounted for rotation to the housing and driven by a motor. A massage node and a positive temperature coefficient (PTC) heater are mounted to the substrate. A pair of contacts and a pair of brushes maintain electrical engagement of the PTC heater with the housing during rotation of the substrate. Another embodiment provides an infrared light emitting diode (LED) beneath the massage node in electrical communication with the housing due to the contacts and brushes. Another embodiment provides a method for imparting a heated massage effect by providing a massage apparatus with a message mechanism, a PTC heater and a plurality of infrared LEDs. A massage effect is imparted and a warm-up operation is initiated of the PTC heater and the LEDs. The warm-up operation of the PTC heater is discontinued upon the massage mechanism reaching a predefined temperature.

17 Claims, 7 Drawing Sheets

(56) References Cited

U.S. PATENT DOCUMENTS

| | | |
|---|---|---|
| 7,678,066 B2 * | 3/2010 | Habatjou .................. 601/15 |
| 2002/0111570 A1 * | 8/2002 | Cutler et al. ............... 601/15 |
| 2003/0009117 A1 | 1/2003 | Zou |
| 2003/0120184 A1 * | 6/2003 | Cafaro ...................... 601/15 |
| 2005/0181090 A1 * | 8/2005 | Olaru ........................ 425/549 |
| 2005/0209537 A1 | 9/2005 | Gleason et al. |
| 2005/0209538 A1 | 9/2005 | Lev et al. |
| 2005/0245851 A1 | 11/2005 | Ferber et al. |
| 2006/0211962 A1 | 9/2006 | Ferber et al. |
| 2007/0060851 A1 | 3/2007 | Ferber et al. |
| 2007/0173748 A1 * | 7/2007 | Shin .......................... 601/15 |
| 2007/0282400 A1 * | 12/2007 | Gorham ..................... 607/88 |
| 2008/0195001 A1 * | 8/2008 | Werner ...................... 601/2 |
| 2008/0262397 A1 * | 10/2008 | Habatjou .................. 601/93 |

OTHER PUBLICATIONS

International Search Report and Written Opinion for corresponding Application No. PCT/US2007/083604, mailed May 23, 2008, 8 pages.

International Preliminary Report for corresponding Application No. PCT/US2007/083604, mailed May 20, 2010, 6 pages.

\* cited by examiner

MASSAGE APPARATUS WITH HEATER

BACKGROUND OF THE INVENTION

1. Field of the Invention

Various embodiments of the present invention relate to massagers.

2. Background Art

The prior art has offered various kneading massagers for imparting a rotary kneading or shiatsu massage effect upon a body part of a user. A rotary kneading massager is disclosed in U.S. Pat. No. 7,128,721 B2, which issued to Ferber et al. on Oct. 31, 2006, the disclosure of which is incorporated in its entirety by reference herein.

The prior art has also provided massagers in combination with heating assemblies for imparting a heated massage effect to a user. One such example is U.S. Patent Application Publication No. 2005/0209538 A1, which published to Lev et al. on Sep. 22, 2005, and is incorporated in its entirety by reference herein.

SUMMARY OF THE INVENTION

One embodiment of the invention discloses a massage apparatus having a housing, a motor oriented in the housing, and a substrate mounted to the housing for rotation relative to the housing. The substrate is driven for rotation by the motor. A massage node is mounted to the substrate for providing a massage effect. A positive temperature coefficient (PTC) heater is disposed beneath the massage node. A pair of conductive contacts are mounted to one of the substrate and the housing. A pair of conductive brushes are each in engagement with one of the contacts, and mounted to the other of the substrate and the housing relative to the corresponding contact for maintaining engagement during rotation of the substrate relative to the housing. Two of the contacts and brushes are in electrical communication with the PTC heater for conducting electricity from the housing to the PTC heater.

Another embodiment according to the present invention discloses a massage apparatus having a housing, a motor oriented in the housing, and a substrate mounted to the housing for rotation relative to the housing. The substrate is operably driven for rotation by the motor. A massage node is mounted to the substrate for providing a massage effect. An infrared light emitting diode (LED) is disposed beneath the massage node. A pair of conductive contacts are each mounted to one of the substrate and the housing. A pair of conductive brushes are each in engagement with one of the contacts and mounted to the other of the substrate and the housing relative to the corresponding contact for maintaining engagement during rotation of the substrate relative to the housing. Two of the contacts and brushes are in electrical communication with the LED for conducing electricity from the housing to the LED.

Another embodiment according to the present invention discloses a method for providing a heated massage effect from a motorized massage apparatus. The method provides a massage apparatus with a massage mechanism, a PTC heater, and a plurality of infrared LEDs. A massage effect is imparted from the massage mechanism. A warm-up operation is initiated of the PTC heater and the LEDs. The warm-up operation of the PTC heater is discontinued upon the massage mechanism reaching a predefined temperature.

The above embodiments, and other embodiments, features, benefits, and advantages of the present invention are readily apparent from the following detailed description of embodiments of the invention when taken in connection with the accompanying drawings.

DESCRIPTION OF EMBODIMENTS OF THE INVENTION

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
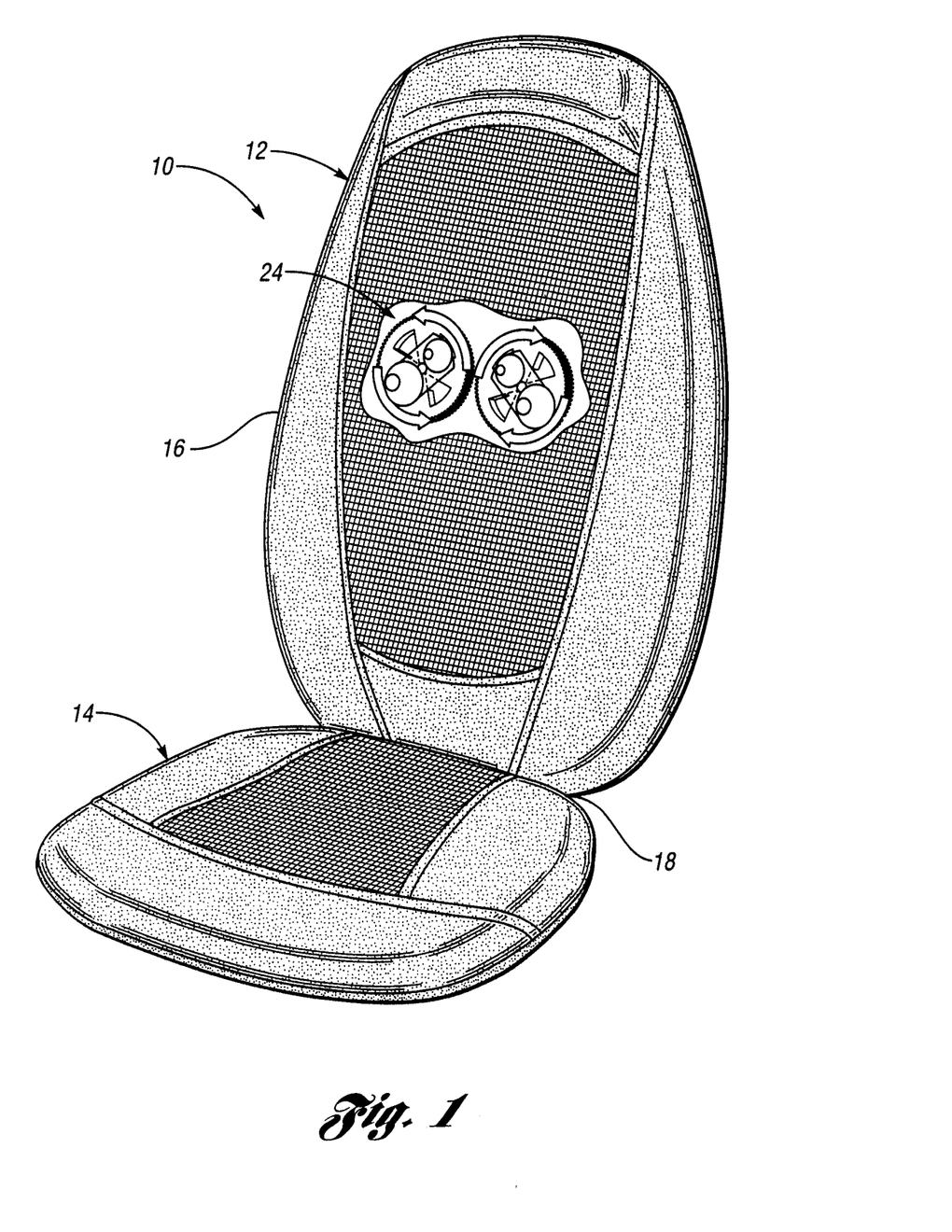
FIG. 1 is a perspective view of a body massager in accordance with an embodiment of the present invention.

With reference to FIG. 1, a body massager is illustrated in accordance with an embodiment of the present invention and is referenced generally by numeral 10. The body massager 10 includes a backrest region 12 and a seat support region 14. The internal assemblies of the backrest region 12 and the seat support region 14 are collectively retained within a flexible cover 16, which is formed of a high quality vinyl. Of course, other materials such as leather may be employed for the cover 16. The cover 16 provides a pivotal connection 18 at a lower longitudinal end of the backrest region 12 and a rearmost end of the seat support region 14. The flexible material of the cover 16 provides a living hinge at the pivotal connection 18 permitting user adjustment of an included angle between the backrest region 12 and the seat support region 14.

Massage effects provided by the body massager 10 include a kneading massage effect provided in the backrest support 12, which is operable to provide the kneading massage effect longitudinally along the length of the backrest region 12. A rotary kneading massage effect that is provided longitudinally along the backrest region 12 is disclosed in U.S. Pat. No. 7,128,721 which has been incorporated by reference herein. The seat support region 14 may provide a vibratory massage effect to the user.

Figure 2:
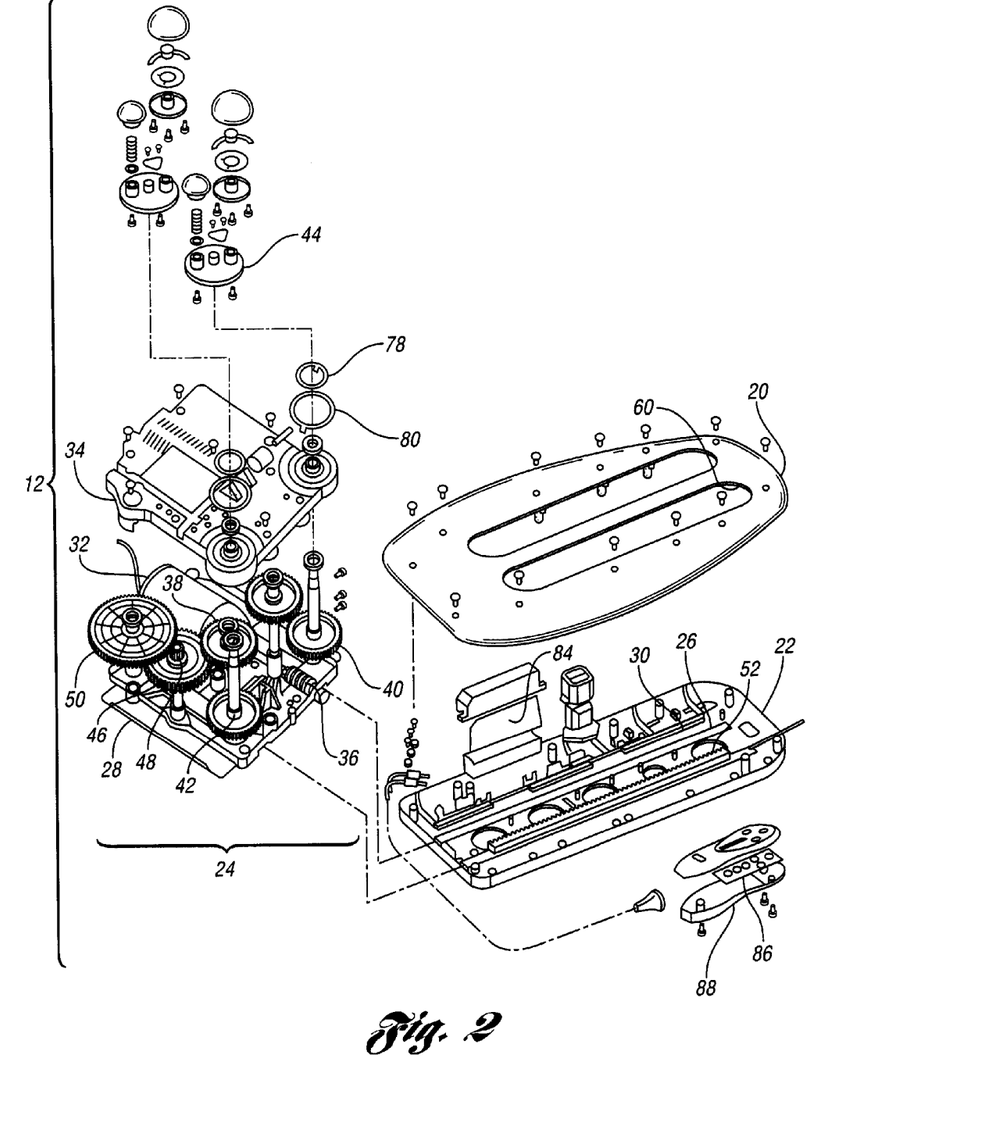
FIG. 2 is an exploded perspective view of a backrest region of the body massager of FIG. 1.

Referring now to FIG. 2, the backrest region 12 is illustrated in greater detail. The backrest region 12 includes a forward housing portion 20 and a rearward housing portion 22 for retaining a massage assembly 24 therein. The rearward housing portion 22 includes a guide 26 for guiding a carriage 28 of the massage assembly 24 longitudinally along the guide 26. The rearward housing portion 22 includes a series of gibs 30 for retaining the carriage 28 against the guide 26.

The carriage 28 includes a motor 32 that is retained to the carriage 28 by a cover plate 34. The motor 32 drives a worm 36, which consequently drives a pair of worm gears 38. Each of the worm gears 38 drive a spur gear 40 that drives a corresponding gear shaft 42 that extends through the cover plate 34. Each of the gear shafts 42 drive a massage bracket 44 in opposed rotation for generating a rotating massage effect.

One of the worm gears 38 also includes a spur gear (not shown) underneath, which is engaged with and drives a reduction gear 46. A spur gear 48 of reduced diameter is mounted to the reduction gear 46 engaged with a second reduction gear 50 for driving the second reduction gear 50 with reduced rotation. The second reduction gear 50 is engaged with a gear rack 52 formed on one of the retainer gibs 30. Thus, as the motor 32 drives the worm 36, the massage brackets 44 are driven in reverse rotation and the carriage 28 is driven longitudinally along the guide 26. Although a massager 10 with a carriage 28 is illustrated and described, the invention contemplates utilization of a massage assembly in a stationary housing, that does not translate relative to another housing.

Figure 3:
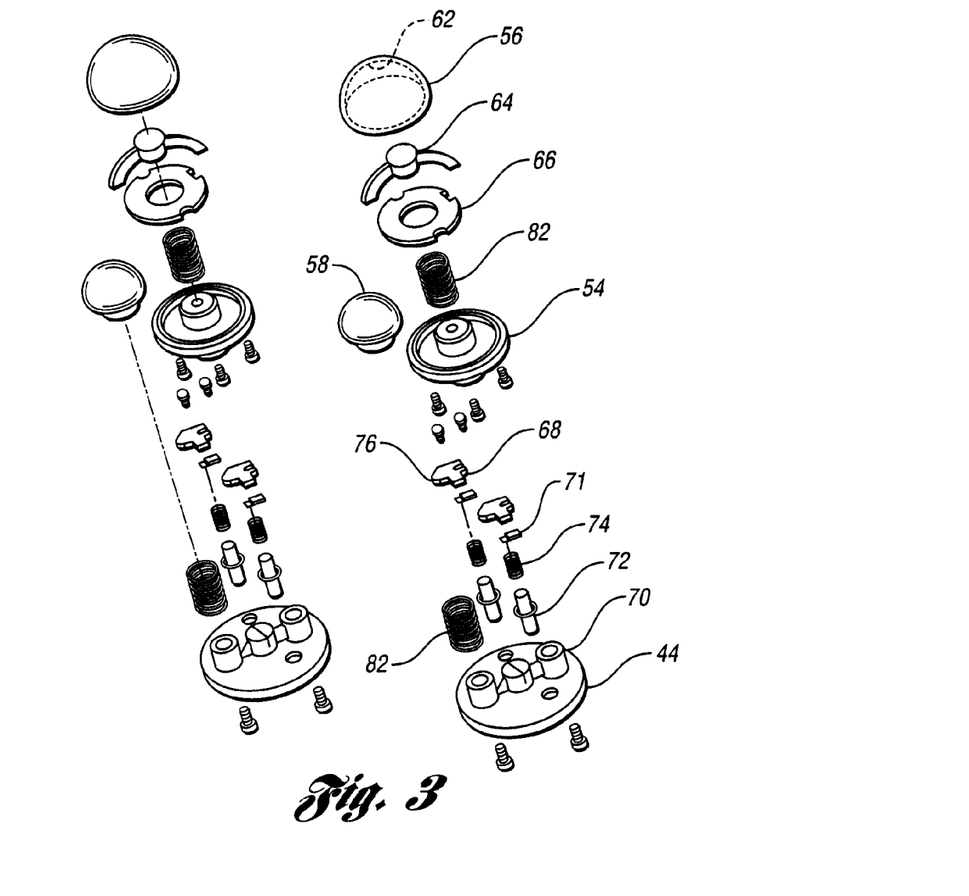
FIG. 3 is an enlarged exploded perspective view of a portion of a massage assembly of the body massager of FIG. 1.

Referring now to FIG. 3, output massage formations of the massage assembly 24 are illustrated in greater detail. A retainer bracket 54 is mounted to each massage bracket 44. A primary massage node 56 is mounted to each retainer bracket 54. In one embodiment, the retainer bracket 54 is formed from a thermal plastic material. A secondary massage node 58 is also mounted to the massage bracket 44. The massage nodes 56, 58 each extend through one of a pair of longitudinal apertures 60 (FIG. 2) formed through the forward housing portion 20 for imparting a rotary kneading massage effect upon the body part of the user. The primary massage node 56 and the secondary massage node 58 are each offset from the corresponding gear shaft 42 to provide the rotary kneading massage effect as the massage bracket 44 is rotated relative to the carriage 28.

Figure 4:
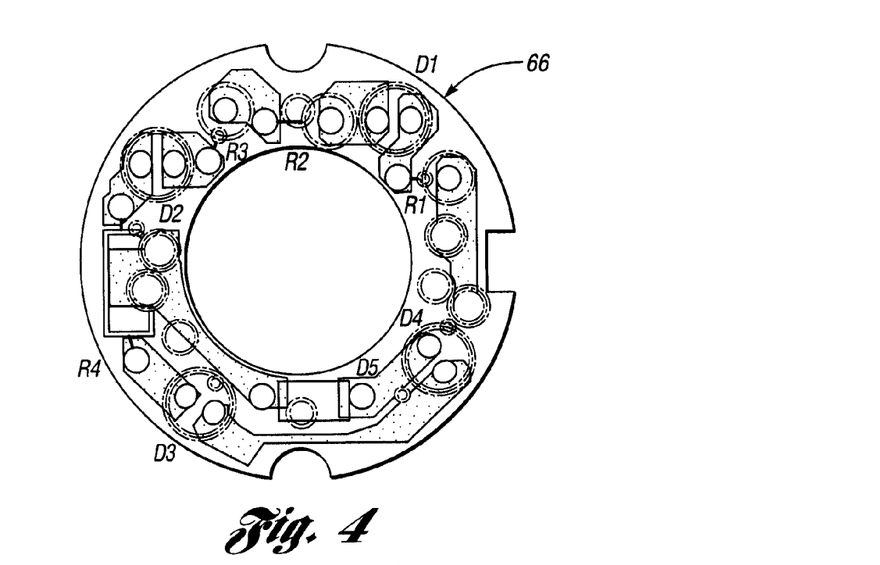
FIG. 4 is an enlarged plan view of a circuit board of the massage assembly of FIG. 1.
Figure 5:
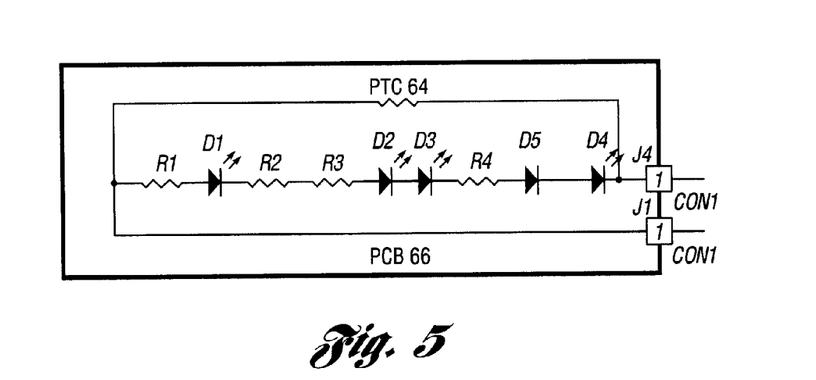
FIG. 5 is a schematic illustrating the circuit board of FIG. 4.

The primary massage nodes 56 each have a cavity 62 formed therein for receiving a heater. In one embodiment, the heater is a positive temperature coefficient (PTC) heater 64 that is disposed within the cavity 62 of the primary massage node 56. In at least one embodiment, the PTC heater 64 is mounted to a printed circuit board 66 that is mounted to the retainer bracket 54. The printed circuit board 66 for at least one embodiment is illustrated in FIGS. 4 and 5 with the PTC heater 64 connected at points P1 and P2. A plurality of infrared light emitting diodes (LEDs) D1, D2, D3, D4 are also mounted to the printed circuit board 66. The infrared LEDs D1-D4 are in series; and the LEDs D1-D4 and the PTC heater 64 are in parallel.

The printed circuit board 66 is wired to a pair of brush assemblies 68, 70. Each brush assembly 68, 70 retains a contact 71 that is wired to the printed circuit board 60. Also, each brush assembly 68, 70 includes a contact pin 72 that extends through the bottom of the massage bracket 44. The contact pins 72 are urged downward by a spring 74. A cap 76 of the brush assembly is fastened to the massage bracket 44 for retaining the spring 74, which urges the contact pins 72 downward and for maintaining electrical communication between the wiring from the printed circuit board 66 and the contact pin 72. Each contact pin 72 may include an enlarged diameter for retaining the pin 72 relative to the massage bracket 44.

Referring again to FIG. 2, a pair of annular contact plates 78, 80 are mounted to the cover plate 34 beneath each massage bracket 44. The contact pin 72 of each brush assembly 70 is urged into engagement with one of the contact plates 78, 80. The contact plates 78, 80 are each wired to selectively provide a source of electrical power to the heaters 64, D1-D4. Since the contact pins 72 are maintained in engagement with the contact plates 78, 80 as the pins 72 are rotated about the gear shaft 42 due to the rotation of the gear shaft 42 and the massage bracket 44, electrical power can be maintained to the heaters 64, D1-D4.

Referring again to FIG. 3, each primary massage node 56 is jointly heated by the PTC heater 64 and the array of the infrared LEDs D1-D4. Although the PTC heater 64 is illustrated as being generally arcuate, any shape is contemplated. The PTC heater 64 is oriented directly below the primary massage node 56 for transferring heat to the primary massage node 56. The LED array D1-D4 is provided by four equally spaced infrared LEDs mounted to the generally circular printed circuit board 66. Each LED is D1-D4 can be further and individually adjusted to focus the heat output into the primary massage node 56 with adjustment of the LEDs D1-D4 light output angle. The result is that the heat from the PTC heater 64 and from each LED D1-D4 can be uniformly overlapped on the underside of the primary massage node 56 or focused on specific regions of the primary massage node 56. In one embodiment, the primary massage nodes 56 are formed from a thermal plastic material to provide a comfortable and soothing rotary kneading massage effect, while concurrently conveying a heating massage effect.

The combination of the PTC heater 64 and the infrared LED D1-D4 array rapidly convey heat to the primary massage nodes 56 and consequently to the user. Alternatively, the primary massage nodes 56 can be heated by the PTC heater 64 alone, or the LED D1-D4 array alone.

Infrared rays allow heat to penetrate deep underneath the surface of the skin, causing the pores of the skin to be opened and promoting metabolism and excretion of the body through increased blood circulation. Additionally, heating massage effects relieve tired muscles and promote circulation of the blood, thereby comforting and relaxing the user. However, infrared LEDs D1-D4 do not rapidly heat the thermal plastic primary massage node 56. In contrast, the PTC heater 64 rapidly heats the thermal plastic primary massage node 56. Thus, the PTC heaters 64 are utilized in combination with LED arrays D1-D4 so that the PTC heaters 64 rapidly heat the primary massage nodes 56 for a rapid heated massage effect. For example, the PTC heaters 64 heat the primary massage nodes 56 to a desired heated massage temperature within one minute. Once the desired massage temperature is reached, the operation of the PTC heater 64 is discontinued. At that point, the infrared array D1-D4 is utilized for maintaining the massage temperature of the primary massage node 56.

Referring again to FIG. 3, in the embodiment depicted, the secondary massage nodes 58 do not include a heater. Thus, a massage effect is provided with both a heated massage node 56 and an unheated massage node 58. Thus, if the user intends to impart a targeted heating effect, such targeted application may be obtained by controlling the orientation of the primary massage node 56. Alternatively, the invention contemplates that a PTC heater 64 and/or a printed circuit board 66 with an LED array D1-D4 can be provided beneath the secondary massage node 58. To further enhance the rotary kneading massage effect provided by the primary and secondary massage nodes 56, 58, a spring 82 is disposed between the massage bracket 44 and each of the massage nodes 56, 58 for urging the massage nodes 56, 58 into contact with a body part of the user while providing axial compliancy of the massage nodes 56, 58 relative to the massage bracket 44.

Referring again to FIG. 2, the body massager 10 includes a printed circuit board 84 mounted to the rearward housing portion 22 for controlling operations of the massager 10. Likewise, a printed circuit board 86 is provided within a remote controller 88 for controlling user selected operations of the massager 10. The printed circuit boards 84, 86 collectively provide a controller for the massager 10. The controller 88 permits the user to select various massage operations including heating massage, and rotary kneading massage in combination with rolling massage as the carriage 24 translates along the guide 26.

The remote controller 88 also permits the user to select a demonstration mode. Such demonstration modes are useful for familiarizing the user with the operation of the massager 10. The demonstration mode is also useful for demonstrating various massage effects that can be provided from the massager 10, such as at a point of sale display. During such demonstration operations, it is advantageous to quickly provide a heated massage effect to the user to demonstrate the heated massage effect and to inform the user of the operation. Likewise, it is advantageous to rapidly inform a potential consumer of the heated massage effect. Thus, the demonstration operation imparts a massage effect from the massage assembly 24. The demonstration operation also conveys power to the printed circuit board 66 which initiates a warm-up operation of the PTC heater 64 and the LED array D1-D4. Once the primary massage nodes 56 reach the desired temperature, the warm-up operation of the PTC heater 64 is discontinued.

The controller provided by the printed circuit boards 84, 86 may discontinue heat from the PTC heaters 64 by a predetermined period of time. The predetermined period of time may be associated with a period of time required for the LEDs D1-D4 to reach a predefined temperature to maintain the predefined massage heat temperature. Alternatively, the predetermined period of time may be associated with the PTC heater 64 reaching a predefined temperature.

PTC heaters experience an increase in electrical resistance as the temperature is raised. Thus, the PTC heater 64 may discontinue the warm-up operation upon the PTC heater 64 reaching a predefined temperature. Thus, as illustrated in FIGS. 4 and 5, the PTC heaters 64 are each employed in parallel with the array of LEDs D1-D4. Therefore, the printed circuit board 66 can be wired in series thereby only requiring one pair of brush assemblies 68, 70 and one pair of contact plates 78, 80 for powering both the PTC heater 64 and the array of LEDs D1-D4. After warm-up of the heaters 64, D1-D4 is initiated, the PTC heater 64 can shut off upon reaching a predefined temperature, and the LEDs D1-D4 continue to operate as they are in parallel with the PTC heater 64. If the temperature drops, the resistance of the PTC heaters 64 drops, and the PTC heaters will provide heat again until the PTC heater reaches the predefined temperature.

Figure 6:
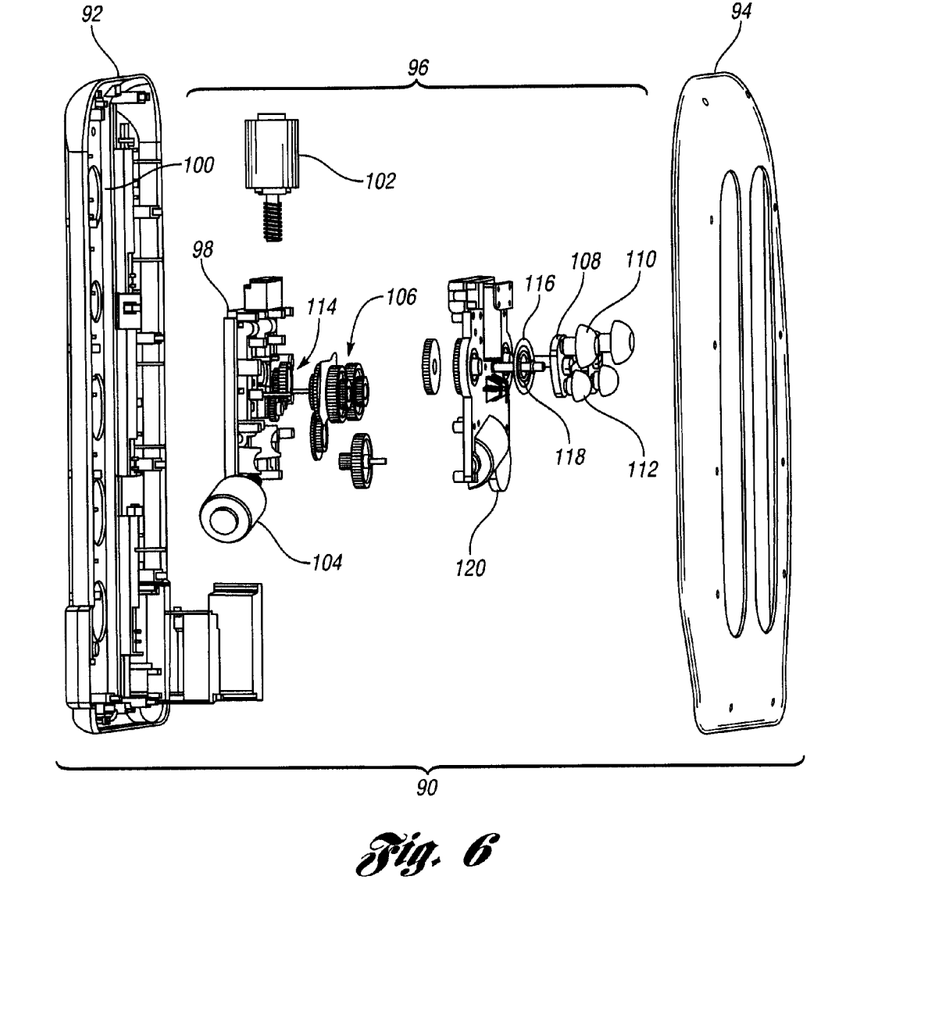
FIG. 6 is an exploded perspective view of a backrest region of a body massager in accordance with another embodiment of the present invention.

Referring now to FIG. 6, another embodiment body massager 90 is illustrated. The body massager 90 is a two motor design similar to that disclosed in U.S. Patent Application Publication No. 2006/0211962 A1, which published on Sep. 21, 2006 to Ferber et al. and is incorporated in its entirety by reference herein. The massager 90 includes a rearward housing portion 92 and a forward housing portion 94. A massage assembly 96 includes a carriage 98 for translating along a guide 100 in the rearward housing portion 92. The carriage 98 includes a first motor 102 and a second motor 104 for separately driving the massage and translation operations. The first motor 102 drives a first transmission 106 for driving a pair of massage brackets 108 in reverse rotation. Each of the massage brackets 108 is provided with a primary massage node 110 and a secondary massage node 112 for collectively providing a rotary kneading massage effect. The second motor 104 drives a second transmission 114 for driving the carriage 98 along the guide 100. Similar to the prior embodiment, each of the primary massage nodes is provided with a PTC heater 64 on a printed circuit board 66 that also includes an array of infrared LEDs D1-D4. A pair of brush assemblies 68 are mounted to the massage brackets 108 in electrical communication with the printed circuit board 66 for engaging a pair of contact plates 116, 118 that are provided on a cover plate 120 of the massage assembly 96.

By utilizing separate motors 102, 104 for controlling the translation and the rotary kneading massage separately, a user may selectively adjust a longitudinal position of the primary massage nodes 110, as well as a rotary orientation, thereby controlling a width of the primary massage nodes 110. Thus, the user can selectively control the placement of the heaters 64, D1-D4 to a targeted area of the body part. Additionally, the user may selectively operate one or both motors 102, 104 for receiving a longitudinal rolling massage effect, a rotary kneading massage effect, or a combination longitudinal rotary kneading massage effect. Each of these massage effects may be provided with or without the heating operation.

Figure 7:
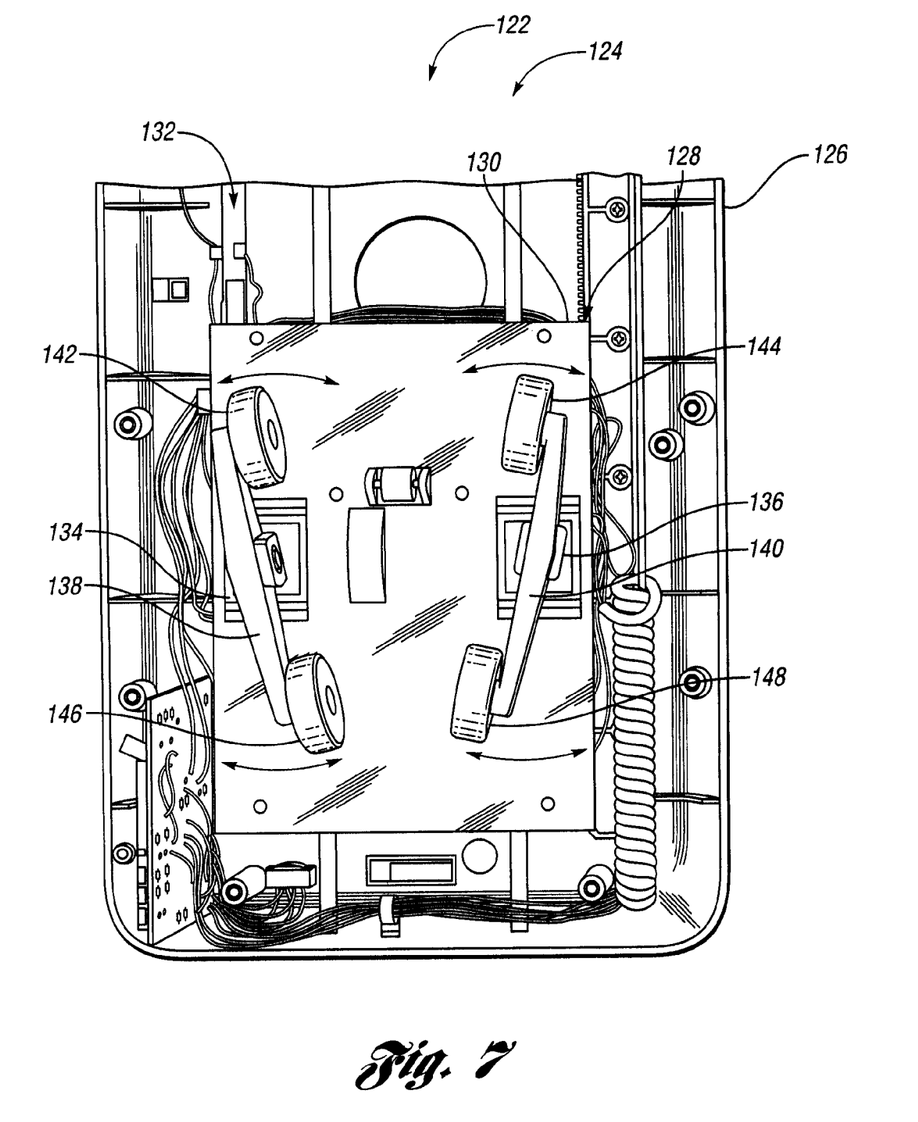
FIG. 7 is an enlarged partial front perspective view of a backrest region of a body massager in accordance with another embodiment of the present invention, illustrated partially disassembled.

Referring now to FIG. 7, a body massager 122 is illustrated according to another embodiment of the present invention. A backrest region 124 of the body massager 122 is partially illustrated with a forward housing portion removed for revealing a rearward housing portion 126. A massage assembly 128 includes a carriage 130 mounted to a guide 132 of the rearward housing portion 126. The body massager 122 is similar to that disclosed in U.S. Patent Application Publication No. 2007/0060851 A1, which published on Mar. 15, 2007 to Ferber et al., which is incorporated in its entirety by reference herein.

The massage assembly 128 includes a pair of oscillating mechanisms 134, 136 for oscillating a pair of massage arms 138, 140. Each massage arm 138, 140 includes an upper roller 142, 144 and a lower roller 146, 148, which are oscillated by the massage arms 138, 140 as indicated by the arcuate arrows in FIG. 7. Thus, the massage assembly 128 provides a kneading massage effect as the rollers 142, 144, 146, 148 are oscillated relative to the carriage 130. Additionally, the massage assembly 128 provides a rolling massage effect as the carriage 130 is translated along the guide 132. Additionally, the massage assembly 128 also provides a rolling and kneading massage effect as the carriage 130 is translated along the guide 132 while the rollers 142, 144, 146, 148 are oscillated.

Figure 8:
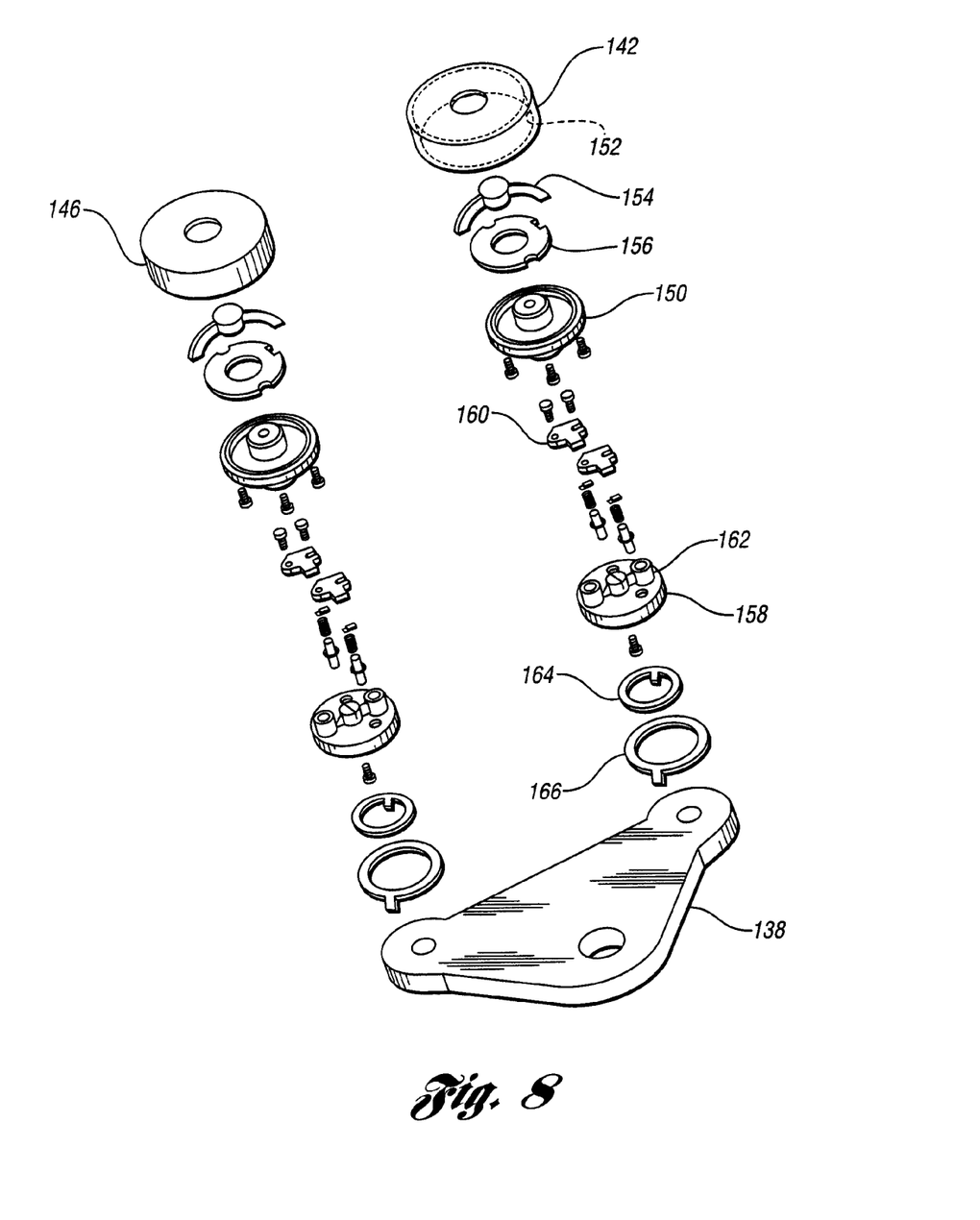
FIG. 8 is an exploded perspective view of a portion of a massage mechanism of the body massager of FIG. 7.

Referring now to FIG. 8, one of the massage arms 138 and the associated rollers 142, 146 are illustrated exploded for revealing underlying components. Each of the rollers 142, 146 is mounted to a thermal plastic retainer bracket 150. Each roller 142, 146 includes a cavity 152 for receiving a PTC heater 154 and a printed circuit board 156, which includes infrared LED array D1-D4. The PTC heater 154 is mounted to the printed circuit board 156 and the printed circuit board 156 is fastened to the retainer bracket 150. Each of the retainer brackets 150 is mounted to a massage bracket 158 that is mounted for rotation on the corresponding massage arm 138. A pair of brush assemblies 160, 162 are mounted to the massage bracket 158. A pair of contact plates 164, 166 are mounted to the massage arm 138 beneath each massage bracket 158. The brush assemblies 160, 162 each engage one of the contact plates 164, 166. Thus, as the rollers 142, 146 roll along a body part of a user, the massage brackets 158 rotate relative to the massage arm 138 and the heaters 154, D1-D4 maintain electrical communication with the associated power circuit due to the engagement of the brush assemblies 160, 162 with the annular contact plates 164, 166 as the brush assemblies 160, 162 rotate with the rotation of the massage bracket 158.

The rapid heat transfer provided by the combination of the PTC heater 154 and the array of infrared LEDs D1-D4 can be utilized in combination with a rolling kneading massager as illustrated for the body massager 122 of FIGS. 7 and 8.

Figure 9:
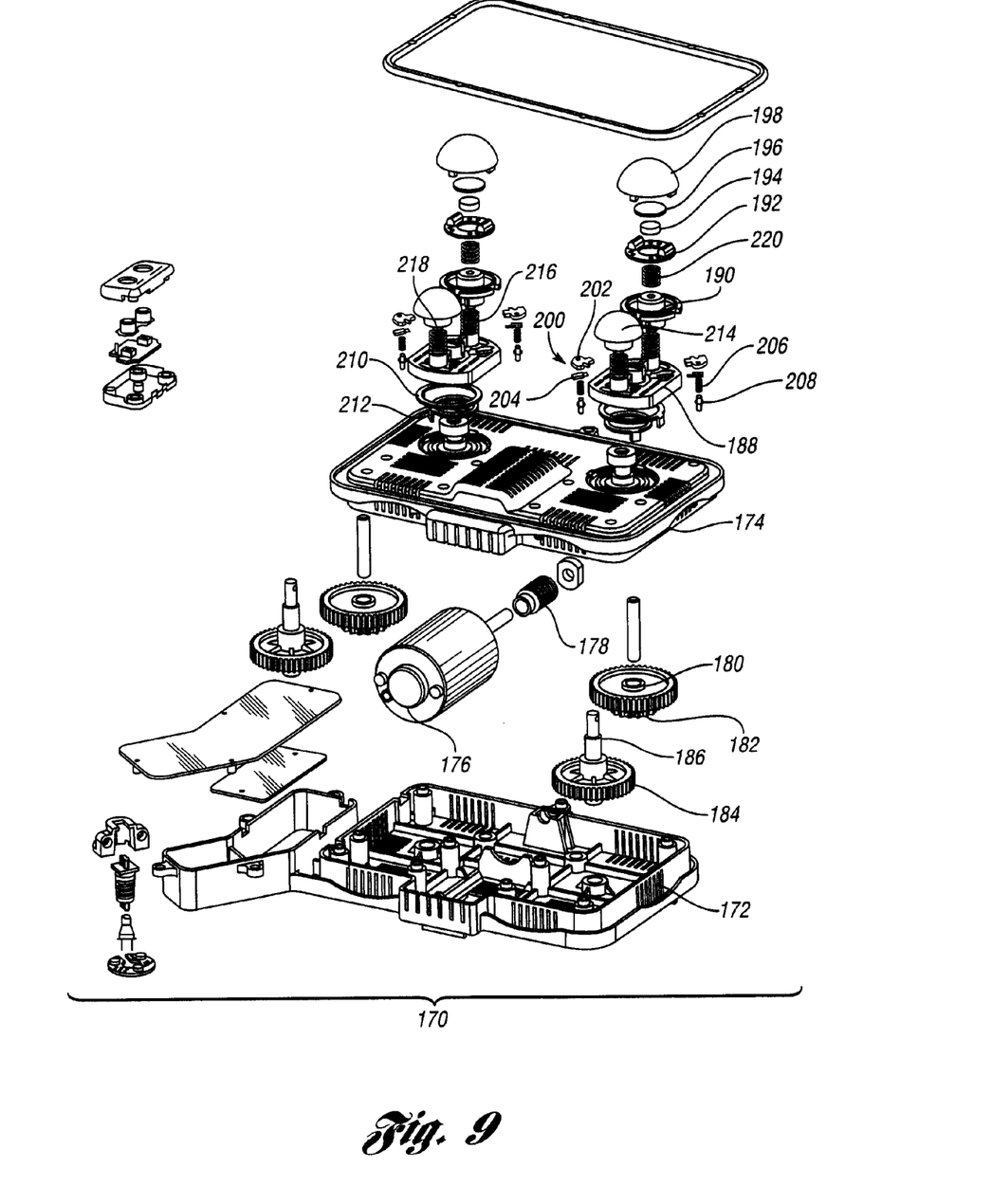
FIG. 9 is an exploded perspective view of a body massager in accordance with another embodiment of the present invention.

FIG. 9 illustrates another body massager 170 having a rearward housing portion 172 and a forward housing portion 174. A motor 176 is retained within the housing portions 172, 174 for driving a worm 178. The worm 178 is engaged to a pair of worm gears 180 for driving the worm gears 180 in a reverse rotary direction. Each of the worm gears 180 includes a spur gear 182 formed on the underside, which is engaged with a reduction gear 184. Each of the reduction gears 184 is mounted to a gear shaft 186 that extends through the forward housing portion 174. A massage bracket 188 is mounted to each gear shaft 186 and driven thereby. A retainer bracket 190 is mounted to each massage bracket 188 offset from the axis of rotation provided by the associated gear shaft 186. A printed circuit board 192 is mounted to each retainer bracket 190 and includes an LED array D1-D4 of infrared LEDs for providing the infrared heating effect. A PTC heater 194 is also mounted to the printed circuit board 192. A conduction plate 196 is provided upon the PTC heater 194 and a primary massage node 198 is mounted to the retainer bracket 190 with the LED array D1-D4, PTC heater 194 and conduction plate 196 housed within the primary massage node 198.

The printed circuit board 192 is wired to a pair of brush assemblies 200 that are mounted to the massage bracket 188. Each brush assembly 200 includes a cap 202 for retaining a contact 204 that is wired to the printed circuit board 192. A spring 206 is disposed beneath the contact 204 for extending a pin 208 to the bottom of the massage bracket 188. A pair of annular contact plates 210, 212 are each mounted on the forward housing portion 174 so that the pins 208 of the brush assemblies 200 maintain contact with the contact plates 210, 212 as the massage brackets 188 are rotated relative to the forward housing portion 174. The contact plates 210, 212 are wired to a source of power for powering the printed circuit board 192 and consequently the infrared LED array D1-D4 and the PTC heater 194. A secondary massage node 214 is also provided upon the massage bracket 188 for complimenting the heated rotary massage effect with an unheated rotary massage effect. A spring 216 is mounted beneath the retainer bracket 190 for providing axial compliancy of the primary massage node 198. Likewise, a spring 218 is provided beneath the secondary massage node 214 to provide axial compliancy. Further, another spring 220 is provided between the massage plate 190 and the primary massage node 198 to maintain engagement of the conduction plate 196 within the primary massage node 198.

The body massager 170 illustrates a heated rotary kneading massage effect provided by a stationary housing 172, 174. Thus, the invention contemplates utilization of various heating massage effects including stationary housing and housings that provide a carriage for translating the heated massage effect along a body part of a user.

Although various kneading massage assemblies are illustrated and described, the invention contemplates utilization of the PTC heater in combination with the infrared LED for providing a rapid warm-up of the imparted massage heat operation for various massage assemblies.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A massage apparatus comprising:
    a housing;
    a motor oriented in the housing;
    a substrate mounted to the housing for rotation relative thereto, and operably driven for rotation by the motor;
    at least one massage node mounted to the substrate for providing a massage effect;
    a positive temperature coefficient (PTC) heater disposed beneath the at least one massage node;
    at least one infrared light emitting diode (LED) disposed beneath the at least one massage node,
    a pair of conductive contacts both mounted to the substrate or the housing;
    a pair of conductive brushes each in engagement with one of the contacts and mounted to the substrate when the contacts are mounted to the housing or mounted to the housing when the contacts are mounted to the substrate for maintaining engagement during rotation of the substrate relative to the housing, wherein both of the contacts and both of the brushes are in electrical communication with the PTC heater and the at least one LED for conducting electricity from the housing to each of the PTC heater and the at least one LED; and
    a controller for controlling the operation of the massage apparatus, the PTC heater, and the at least one LED, the controller being adapted to:
        receive an input signal for requesting a demonstration operation of the massage apparatus;
        initiate a heating operation of the PTC heater and the at least one LED such that the heating operation of the PTC heater is discontinued upon the massage apparatus reaching a predefined temperature while continuing the heating operation of the at least one LED so as to maintain a heated state of the at least one massage node.

2. The massage apparatus of claim 1 wherein the at least one LED further comprises a plurality of LEDs.

3. The massage apparatus of claim 1 further comprising a circuit board mounted to the substrate, wherein the at least one LED and the PTC heater are connected to the circuit board, and two of the contacts and brushes are in electrical communication with the circuit board for conducting electricity from the housing to the circuit board.

4. The massage apparatus of claim 3 wherein the at least one massage node includes a cavity formed in its underside and the at least one LED is mounted to the circuit board and extends into the cavity.

5. The massage apparatus of claim 1 wherein the pair of conductive contacts are each mounted to the housing, and the pair of conductive brushes are each mounted to the substrate in electrical communication with the PTC heater for conducting electricity from the contacts to the PTC heater.

6. The massage apparatus of claim 5 wherein the contacts are generally annular.

7. The massage apparatus of claim 1 wherein the substrate rotates about an axis and the at least one massage node is offset from the axis and mounted for rotation to the substrate.

8. The massage apparatus of claim 7 wherein the at least one massage node is further defined as a first massage node and the massage apparatus further comprises a second massage node mounted for rotation to the substrate, spaced apart from the first massage node.

9. The massage apparatus of claim 8 wherein the second massage node does not include a heater.

10. The massage apparatus of claim 1 further comprising a thermal plastic bracket mounted to the substrate, wherein the PTC heater and the at least one massage node are mounted to the thermal plastic bracket.

11. The massage apparatus of claim 1 wherein the housing is further defined as a carriage mounted to a guide for translation along the guide.

12. The massage apparatus of claim 1 wherein the at least one massage node includes a cavity formed in its underside and the PTC extends into the cavity.

13. A method for providing a heated massage effect from a motorized massage apparatus comprising:
 providing a massage apparatus comprising:
  a housing;
  a motor oriented in the housing;
  a substrate mounted to the housing for rotation relative thereto, and operably driven for rotation by the motor; and
  at least one massage node mounted to the substrate for providing a massage effect;
  the positive temperature coefficient (PTC) heater disposed beneath the at least one massage node;
  a plurality of infrared light emitting diodes (LEDs) disposed beneath the at least one massage node,
  a pair of conductive contacts both mounted to the substrate or the housing;
  a pair of conductive brushes each in engagement with one of the contacts and mounted to the substrate when the contacts are mounted to the housing or mounted to the housing when the contacts are mounted to the substrate for maintaining engagement during rotation of the substrate relative to the housing, wherein both of the contacts and both of the brushes are in electrical communication with the PTC heater and LEDs for conducting electricity from the housing to each of the PTC heater and the LEDs; and
  a controller for controlling the operation of the massage apparatus, the PTC heater, and the LEDs;
 imparting a massage effect from the massage apparatus;
 initiating a warm-up operation of the PTC heater and the LEDs; and
  discontinuing the warm-up operation of the PTC heater upon the massage apparatus reaching a predefined temperature while maintaining a heated state of the LEDs.

14. The method of claim 13 further comprising discontinuing the operation of the PTC heater upon the LEDs reaching a predefined temperature.

15. The method of claim 14 further comprising discontinuing the operation of the PTC heater upon the PTC heater reaching a predefined temperature.

16. The method of claim 15 further comprising discontinuing the operation of the PTC heater after a predetermined period of time.

17. The method of claim 16 wherein the predetermined period of time is less than one minute.

* * * * *